(12) United States Patent
Lakestani et al.

(10) Patent No.: US 7,364,354 B2
(45) Date of Patent: Apr. 29, 2008

(54) METHOD AND SYSTEM FOR MEASURING THE THERMAL DIFFUSIVITY

(75) Inventors: Fereydoun Lakestani, Varese (IT); Antonio Salerno, Milan (IT); Alberto Volcan, Varese (IT)

(73) Assignee: The European Community (BE)

( * ) Notice: Subject to any disclaimer, the term of this patent is extended or adjusted under 35 U.S.C. 154(b) by 58 days.

(21) Appl. No.: 10/535,073

(22) PCT Filed: Nov. 20, 2003

(86) PCT No.: PCT/EP03/50854

§ 371 (c)(1),
(2), (4) Date: Jan. 27, 2006

(87) PCT Pub. No.: WO2004/046671

PCT Pub. Date: Jun. 3, 2004

(65) Prior Publication Data

US 2006/0153269 A1 Jul. 13, 2006

(30) Foreign Application Priority Data

Nov. 20, 2002 (EP) .................................. 02360318

(51) Int. Cl.
*G01N 25/20* (2006.01)
(52) U.S. Cl. ...................................... 374/43
(58) Field of Classification Search .................. 374/43; 702/136
See application file for complete search history.

(56) References Cited

U.S. PATENT DOCUMENTS

| 4,928,254 | A | * | 5/1990 | Knudsen et al. | ............ 702/136 |
| 5,080,495 | A | * | 1/1992 | Hashimoto et al. | ........... 374/43 |
| 5,586,824 | A | | 12/1996 | Barkyoumb et al. | |
| 5,667,300 | A | * | 9/1997 | Mandelis et al. | ............. 374/43 |
| 5,713,665 | A | | 2/1998 | Kato et al. | |
| 6,260,997 | B1 | * | 7/2001 | Claybourn et al. | ........... 374/45 |
| 6,958,814 | B2 | * | 10/2005 | Borden et al. | .............. 356/432 |

FOREIGN PATENT DOCUMENTS

| EP | 0 419 873 | 3/1991 |
| JP | 62 050652 | 5/1987 |

OTHER PUBLICATIONS

International Search Report; PCT/EP03/50854; Jun. 4, 2004.
Thomas S. et al: "Thermal Diffusivity of Solids by Photoacoustic Cell Rotation and Phase Lag Measurement"; Review of Scientific Instruments, American Institute of Physics. New York, US, vol. 66, No. 7, Jul. 1, 1995, pp. 3907-3908 XP000524293; ISSN:0034-6748.

* cited by examiner

*Primary Examiner*—Gail Verbitsky
*Assistant Examiner*—Megann E Vaughn
(74) *Attorney, Agent, or Firm*—Cantor Colburn LLP

(57) ABSTRACT

The present invention concerns a method and a system for measuring the thermal diffusivity. Said method comprises the steps of: subjecting a surface region of an object to a modulated heating beam (3) while providing a signal (MLS) thereof, the heated spot or area (4) of the surface of the sample (2) having a definitive diameter and a fixed intensity distribution profile; providing a signal (MTS) proportional to the temperature of the heated spot area (4); determining the phase difference between the modulated beam signal (MLS) and the resulting modulated temperature signal (MTS); and using said determined phase difference and the associated frequency to work out the thermal diffusivity value of said object (2).

19 Claims, 1 Drawing Sheet

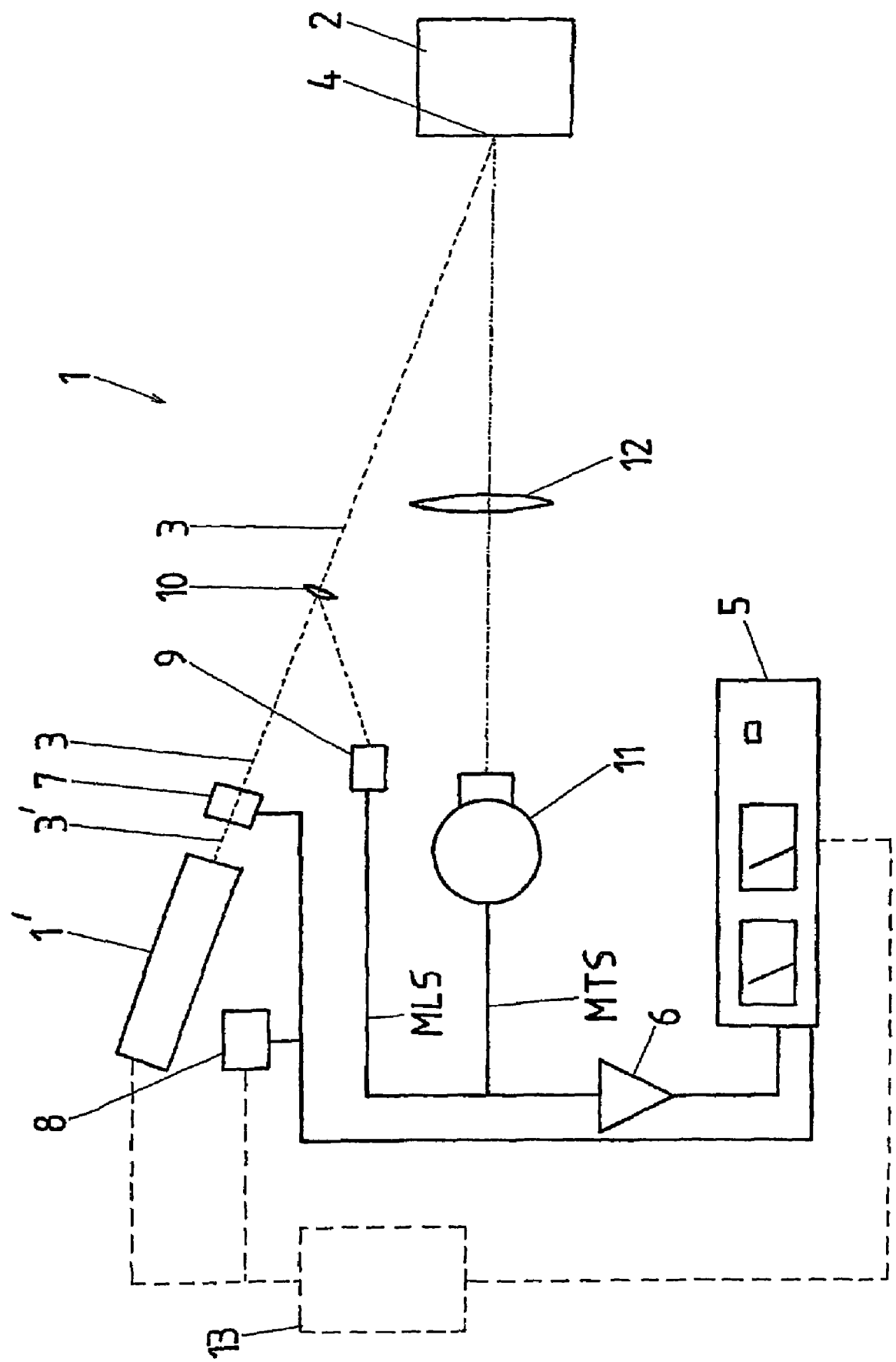

METHOD AND SYSTEM FOR MEASURING THE THERMAL DIFFUSIVITY

TECHNICAL FIELD OF THE INVENTION

The present invention is related to the measurement of physical properties of materials, components or articles, and concerns a method for measuring the thermal diffusivity and a corresponding system able to perform such a measurement.

BRIEF SUMMARY OF RELATED ART

The thermal diffusivity is a material thermal property which is important in many engineering applications.

Various methods are already known in order to perform such measurements, the two most efficient and precise ones using laser based techniques.

Thus, a first known method of this type is the so-called "Laser flash" method.

In this latter method, a sample of the material to be investigated must be prepared. Furthermore, two opposite sides of said sample must be parallel and its thickness known with high precision.

The sample is then uniformly heated by a laser pulse on one side. On the opposite side of this sample an IR detector measures the temperature rise. The rise time of the temperature is linked to the thermal diffusivity which can thus be determined.

Nevertheless, this first known method shows a number of disadvantages and restrictions when it is practically implemented, among which one can cite: the measurement can not be performed on a bulk; a sample must be extracted and accurately prepared; two faces of the sample need to be parallel and accessible.

A second known method of the aforementioned type is the so-called "3D-Photothermal radiometry".

In this second method, the sample is heated by a focused modulated laser beam and on the same side of the sample an infrared detector (IR-detector) measures the modulated surface temperature at an increasing distance from the heated spot. The phase difference between the modulated laser and the modulated temperature depends on this distance and on the thermal diffusivity of the material.

However, this latter method does also present certain disadvantages in connection with its practical implementation, as the laser spot or the IR-detector must be moved, as the IR and visible optic need an extremely accurate preparation, and as the IR signal becomes rapidly very weak as the distance from the heated spot increases.

BRIEF SUMMARY OF THE INVENTION

Therefore, the present invention provides a method for measuring the thermal diffusivity characterized in that it comprises the steps of:

subjecting a surface region of the object, whose thermal diffusivity has to be determined, to a modulated laser beam or to the modulated beam of a similar heating source while providing a signal thereof by, for example, measuring said beam and providing a signal proportional to the beam intensity, the heated spot or area of the surface of the object having a definitive diameter and a fixed intensity distribution profile;

providing a signal proportional to the temperature on the heated spot or area;

determining the phase difference or phase shift between the modulated beam signal and the resulting modulated temperature signal;

using said determined phase difference or shift and its associated modulation frequency to work out the thermal diffusivity value of said object.

Providing a signal of the modulated beam applied to the surface region does not necessarily mean to measure said beam itself. For example, a small part of the beam can be deviated and a signal proportional to said beam extracted from it.

Furthermore, it is neither necessary to measure the temperature of the heated spot or area. It is enough to provide a signal proportional to said temperature or with the same frequency and phase than said temperature.

The invention takes advantage of the fact that:

given a fixed spatial distribution of an amplitude-modulated beam, e.g. a laser beam, heating the flat surface of an object;

given a fixed spatial sensitivity distribution of a surface temperature measurement system, e.g. infrared detector, providing a temperature signal;

the phase lag of the temperature signal with respect to beam modulation signal depends only on the diffusion length of the heated material.

DETAILED DESCRIPTION OF THE INVENTION

On two different materials with respective diffusivities $\alpha 1$ and $\alpha 2$, the same phase lag is obtained at two different modulation frequencies $f1$ and $f2$ such that the corresponding diffusion lengths $\mu 1$ and $\mu 2$ are equal. Knowing that $\mu^2 = \alpha/(\pi)f$, where $\alpha$ is the diffusivity, it follows that $\alpha 1/f1 = \alpha 2/f2$.

The phase lag being measured on a reference material with well-known diffusivity, the diffusivity of the second material is retrieved from the above-mentioned formula.

The above-mentioned technique does not require the knowledge of the sensitivity and beam spatial distributions but requires a reference material. Alternatively, if the distributions are known, the absolute diffusion length can be theoretically determined measuring the phase lag at one or multiple modulation frequencies, without needing a reference material.

Since the measurement can be performed on a bulk, there is no need of extracting a sample. The measurement can be directly performed on a surface point of the object of interest. If one wants to measure the thermal diffusivity of a point on the surface, for instance, of a turbine, blade, said blade is taken, put it in the right position in the measuring apparatus and the measure of its diffusivity on the desired point is performed.

One can also imagine that the measuring apparatus or system can be made so small and compact, that the system itself is taken (instead of the blade), put it in contact with the surface of the blade and the diffusivity of the desired point measured.

Advantageously, at least one modulation parameter can be subjected to controlled variation, preferably the frequency, which allows an accurate modulation and detection of said modulation.

In theory, if a semi-infinite solid is sinusoidally heated on a dimensionless surface point, the temperature of this point has a 0° phase shift with the heating source. On the other hand, if a semi-infinite solid is sinusoidally heated, in a homogeneous way on its surface, the phase shift with the heating source is −45°.

In practice, the surface is heated by a beam such as a laser with a given intensity distribution profile on a spot of finite dimension. Depending on the modulation frequency this situation can be similar to the point heating or to the homogeneous heating.

If the thermal diffusion length $\mu$ ($\mu=\sqrt{\alpha/\pi f}$, where $\alpha$ is the thermal diffusivity and f is the modulation frequency) is small with respect to the diameter of the region heated by the beam, the situation is similar to the homogeneous heating.

If the thermal diffusion length $\mu$ is big, compared with the diameter of the region heated by the laser, the situation is similar to the point heating with a phase shift of 0°.

While the frequency is varied, the phase shift changes from 0° to −45°.

The knowledge of the intensity distribution profile of the laser beam Q and the knowledge of the sensitivity profile P of the temperature measuring system, for example an IR detection system (IR detector and its lens), would allow to reckon the thermal diffusivity $\alpha$, having measured the dependence of the phase shift $\Delta\phi$ from the modulation frequency f. The intensity distribution profile of the laser or heating beam and the sensitivity profile of the IR detecting system play the same role and only the profile, obtained with the convolution of the two, influences the measurement. If the two profiles are changed, but their convolution remains the same, the measurement does not change. These two profiles are in general not well known and change if something in the measurement set-up is moved.

Since the object on which to perform the measurement is always placed in the same position and nothing moves during the measurement, the two profiles Q and P remain always the same. The dependence of the phase shift from the modulation frequency can be recorded for a reference sample, with known thermal diffusivity $\alpha_r$.

According to a simple and preferred embodiment of the invention, the thermal diffusivity value $\alpha_m$ of the analysed object is evaluated by comparison with at least one reference or reference sample whose thermal diffusivity value $\alpha_r$ has been determined previously or is known and which has been subjected to the same measurement method in similar conditions of analysis.

Furthermore, the temperature is preferably, but not necessarily, measured at the center of the heated spot or area, which allows to collect a stronger signal.

Thus, the same measurement, as for the reference, is performed on the object of interest and the results compared with the ones obtained for the reference, in order to work out the value of thermal diffusivity $\alpha_m$ of said object. In this way, the knowledge of the two profiles Q and P is not necessary. Therefore, they can remain unknown, but they must remain the same for the measurements of all objects to be analysed.

Let assume that the curve "phase shift vs. modulation frequency" has been recorded for a reference sample. The shape of this curve in a logarithmic frequency scale is a straight line. If, for instance, the measurement is performed on an object and, for a certain modulation frequency of the heating source, a phase shift of −30° is measured, this phase shift is compared with the results obtained on the reference sample. Knowing the frequency at which the phase shift −30° was obtained for the reference sample, which has a known thermal diffusivity, the thermal diffusivity for the object of the measurement can be worked out, knowing that, when the two phase shifts are the same: $\alpha_r/f_r = \alpha_m/f_m$ (1) where $\alpha$ is the thermal diffusivity, f the modulation frequency, "r" refers to "reference sample" and "m" refers to the object on which the measurement was performed.

In a first alternate carrying out of the said preferred embodiment, the modulation frequency of the heating beam is varied and the variation of the phase shift with respect to the heating source is recorded for a plurality of modulation frequencies. Since the resulting curve in a diagram with logarithmic frequency scale, is a straight line parallel to the one obtained for the reference sample, one can obtain the value of thermal diffusivity by measuring the shifting required to superimpose the two curves.

In a second alternate carrying out of the said preferred embodiment, the modulation frequency is not varied and the phase shift is recorded at a given frequency $f_m$. The dependence of the phase shift from the modulation frequency for the reference sample has been previously measured. The value of the modulation frequency $f_r$ yielding the same phase shift for the reference is taken. Since the two phase shifts are the same, formula (1) allows to reckon the thermal diffusivity $\alpha_m$ of the object to be measured knowing the thermal diffusivity $\alpha_m$ of the reference.

In a third alternate carrying out of the said preferred embodiment, the modulation frequency is varied till the phase shift reaches a predefined value obtained for the reference sample. Formula (1) is then applied to determine $\alpha_m$.

In order to be able to perform measurements with high accuracy without needing accurately adjusted sensing and measuring means, the invention proposes advantageously that the modulated beam signal and the modulated temperature signal are both measured, successively and possibly repetitively, by preferably the same path and means, such as for example a lock-in amplifier preceded by a preamplifier, for example by masking alternatively the beam signal generator and the temperature signal generator. The used path and means add their own phase shift that is eliminated using the same path and means. If different measurement path and means are used, the inserted phase shift by the measurement system at each frequency should be known and substracted.

It is worth to notice that the modulated beam signal at a given frequency is independent of the materials under test. Thus, if the instrumentation is stable enough, it can be measured once and memorized for future comparison with the temperature signal. In those conditions, the measurement procedure and the instrumentation might be simplified noticeably.

According to an advantageous feature of the invention, the provided heating beam is modulated by means of an acousto-optical modulator or a mechanical chopper, driven by an adjustable generator.

According to an other feature of the invention, the modulated beam signal is generated by a light sensor, such as for example a photodiode, receiving a deviated part of the beam, for example the light reflected by a lens through which the modulated beam is passing to be focused before striking the sample. The temperature signal is generated by an infrared sensor receiving the radiation sent out by the heated region or spot of the surface of the analysed sample and focused by an infrared lens.

The proposed method allows for thermal diffusivity measurement of a bulk material without the need of preparing a sample with a certain thickness and without the need of measuring the modulated surface temperature at different distances from the heated point. The method is therefore much simpler and versatile than the two aforementioned known methods and can be applied to objects with various surface geometry.

The present invention also provides a system for measuring the thermal diffusivity of an object, said system comprising a laser device or a similar heating source, whose beam is directed towards a region or spot on the surface of said object.

Said system is characterized in that it also comprises means for modulating said laser or heating beam, means for generating a signal corresponding to said modulated laser or heating beam, means for generating a signal corresponding to the modulated temperature of the region or spot striked by the modulated beam and amplifying and measuring means able to determine at least the phase difference or a shift between the modulated beam signal and the resulting modulated temperature signal and possibly the thermal diffusivity value of said object based upon said phase difference.

Preferably, said system is adapted to perform the thermal diffusivity measurement method as described before.

The present invention will be better understood thanks to the following description and drawing of an embodiment of said invention given as non limitative example thereof, the FIGURE of said drawing consisting of a schematic and functional view of a system according to the present invention.

As shown on the enclosed FIG., the thermal diffusivity measurement system 1 mainly comprises a laser device or a similar heating source 1' whose beam 3' is directed towards a region or spot 4 on the surface of a sample 2 to be analysed. Said system 1 also comprises means 7, 8 for modulating said beam 3', a lens 10 for focusing the beam on a spot of desired diameter on the sample surface, a means 9 for generating a signal MLS corresponding to the modulated laser beam 3, means 11, 12 for generating a signal MTS corresponding to the modulated temperature of the region or spot 4 striked by the modulated beam 3 and amplifying and measuring means 5, 6 able to determine at least the phase difference or shift between the modulated beam signal MLS and the resulting modulated temperature signal MTS and possibly the thermal diffusivity value $\alpha_m$ of said material sample 2 based upon said phase difference.

The sample 2 is preferably heated by a modulated laser beam 3 on a spot 4 of diameter D with fixed intensity distribution profile P. The IR-detector or sensor 11 measures the modulated temperature, preferably at the center of the heated spot 4, as the modulation frequency is varied.

The phase difference between the modulated temperature and the modulated laser depends on the modulation frequency, the diameter D, the intensity distribution profile P and the thermal diffusivity. The heating beam 3' profile and the detector 11 sensitivity profile (i.e. the portion of the sample 2 surface whose emitted infrared radiation strikes the detector 11) play the same role. It follows that the heating spot 4 can be small and the sensitivity profile of detector 11 large.

In practice, the measurement can be performed, for example, by varying the modulation frequency till the phase difference reaches the same value than that obtained for the reference sample.

Since only one surface must be accessible, the measurement can be performed without sample preparation on a bulk. Moreover there is no need of any mechanical displacement of any component. All components of the system 1 remain in the same position and only the modulation frequency is varied.

According to a preferred featuring and implantation of the invention, the measuring means consist of a lock-in amplifier 5 preceded by a preamplifier 6, the provided laser beam 3' is modulated by means of an acousto-optical modulator 7, or a mechanical chopper, driven by an adjustable generator 8 and the modulated laser signal MLS is generated by a light sensor 9, such as a photodiode, receiving part of the light of the beam reflected by the lens 10 through which the modulated laser beam 3 is passing before striking the sample 2.

The temperature signal MTS is generated by an infrared sensor 11 receiving the radiation sent out by the heated region or spot 4 of the surface of the analysed sample 2 and focused and possibly filtered by an infrared lens 12.

As can been seen on the FIGURE, both signals MLS and MTS are preferably, but not necessarily, handled by the same measuring path.

The lock-in amplifier measures the phase of the input signal with respect to a reference signal provided by the generator 8 driving the beam amplitude modulator. The input signal is the sum of the short circuit currents of the photodiode and the infrared detector. These currents are successively zeroed masking the light entering in the photodiode or the infrared radiation entering in the detector. The difference of the measured phases is the phase shift between beam amplitude signal and the temperature signal.

As mentioned before, in case of enough stable instrumentation, the phase of the photodiode signal can be measured once in factory and memorized for future comparison with infrared detector signal, simplifying noticeably the instrumentation, the measurement procedure and the measurement duration.

Optionally, there can also be provided a system controller 13, such as a computer unit, which can analyse the results delivered by the measuring means 5, 6 and possibly drive the CW-generator 8 and the laser device 1'.

In an experimental set-up made by the inventors, the laser beam (0.5 mm-6 dB beam diameter) and the detector beam (2 mm-6 dB beam diameter), i.e. the portion of the sample surface whose emitter infrared radiation strikes the detector 11, were equicentered. This yields a stronger signal.

The modulation of the laser beam 3' is measured by a photodiode 9 connected to the amplifier 6 in parallel to the IR detector 11. The short circuit current from the photodiode 9 and from the detector 11 are assumed to be proportional to the laser intensity and the IR radiation from the surface.

Hence, masking successively the photodiode 9 and the IR detector 11, the phase of the laser modulation and that of the Ir radiation are measured by the same electronic arrangement 5 and 6. It follows that the phase difference was measured without ambiguity. In this configuration the phase difference is zero for low frequencies and decreases progressively down to −45° at high frequencies.

As explained herein before, when presented in a logarithmic scale, the phase curves of various materials are obtained from a simple horizontal shift. The shift in logarithmic frequency scale expresses a ratio that is simply equal to the ratio of the thermal diffusivity of the two materials. A way to measure the diffisivity is to determine the shift that yields the best fit with the phase curve from Poco-graphite chosen as reference material.

Since the experimental set-up remained unchanged, the diameter of the laser beam and the detector sensitivity profile did not need to be known. It was only important that, for the range of frequencies used, a sufficient phase variation was obtained allowing the best fitting operation.

As for the advantages of the present invention, it should be noted that, in comparison to the "Laser flash" method, the inventive method does not require that a small sample is taken and prepared for the measurement. It can be performed on bulk components since both heating and radiative temperature measurement are performed on the same side of the sample. This is very important for many engineering applications.

Furthermore, in comparison to the "3D-photothermal radiometry", there is no need to move the sample, the laser beam or the IR detector. Another advantage is that the infrared signal is much stronger since the measurement is performed directly on the heated spot. This implies that the uncertainties due to random noises are lower.

The present invention is, of course, not limited to the preferred embodiment described and represented herein, changes can be made or equivalents used without departing from the scope of the invention.

The invention claimed is:

1. Method for measuring the thermal diffusivity of an object, said method comprising:
   subjecting a surface region of an object, whose thermal diffusivity ($\alpha_m$) has to be determined, to a modulated laser beam or to a modulated beam of a similar heating source while providing a signal (MLS) thereof, a heated spot or area of the surface of the object having a definitive diameter and a fixed intensity distribution profile;
   providing a signal (MTS) proportional to a temperature on the heated spot or area;
   determining a phase difference or phase shift between the modulated beam signal (MLS) and the resulting modulated temperature signal (MTS);
   using said determined phase difference or shift and an associated modulation frequency to work out the thermal diffusivity value ($\alpha_m$) of said object.

2. Method according to claim 1, wherein said signal (MLS) of said modulated laser beam or modulated beam of a similar heating source is provided by measuring said beam and providing a signal proportional to a beam intensity.

3. Method according to claim 1, wherein at least one modulation parameter is subjected to controlled variation, and wherein the temperature is measured at the center of the heated spot or area.

4. Method according to claim 3, wherein said modulation parameter is frequency.

5. Method according to claim 1, wherein the thermal diffusivity value ($\alpha_m$) of the object is evaluated by comparison with at least one reference or reference sample whose thermal diffusivity value ($\alpha_r$) has been determined previously by being subjected to the same measurement method in similar conditions.

6. Method according to claim 5, wherein the modulation frequency of the beam is varied and the variation of the phase shift of the latter with respect to the heating source is recorded for a plurality of modulation frequencies, the value of the thermal diffusivity being determined by measuring the shifting required to superimpose respective curves $\Delta\phi=F(f)$ obtained for the object and a reference sample in a diagram with logarithmic frequency scale, where $\Delta\phi$ is the phase shift and f is the modulation frequency.

7. Method according to claim 5, wherein the phase shift between the modulated beam and the corresponding modulated temperature is recorded for the object at a given modulation frequency ($f_m$), then the value of the modulating frequency ($f_r$) yielding the same phase shift for the reference is determined and finally the value of the thermal diffusivity ($\alpha_m$) of the object is computed using the formula: ($\alpha_m$)=$\alpha_r\times$($f_m/f_r$), the dependence of the phase shift from the modulation frequency for the reference being known or having been previously measured.

8. Method according to claim 5, wherein the modulation frequency ($f_m$) of the beam applied to the object is varied until the phase shift between the modulated heating beam and the corresponding modulated temperature reaches a predetermined value obtained previously for the reference at a given modulation frequency ($f_r$) and that the thermal diffusivity value ($\alpha_m$) of the object is computed using the formula: ($\alpha_m$)=($\alpha_r\times f_m$)/$f_r$, the dependence of the phase shift from the modulation frequency for the reference being known or having been previously measured.

9. Method according to claim 1, wherein the modulated beam signal (MLS) and the modulated temperature signal (MTS) are both measured, successively and possibly repetitively, by measuring path and means.

10. Method according to claim 9, wherein the measuring path and means are the same for both signals.

11. Method according to claim 10, wherein measurement of the modulated beam signal (MLS) and the modulated temperature signal (MTS) is carried out by the same measuring path and means, by masking alternatively the beam signal generator and the temperature signal generator.

12. Method according to claim 10, wherein the measuring path and means include a lock-in amplifier preceded by a preamplifier.

13. Method according to claim 9, wherein the modulated beam signal (MLS) is generated by a light sensor receiving a deviated part of the beam, and wherein the temperature signal (MTS) is generated by an infrared sensor receiving radiation sent out by the heated region or spot of the surface of the analyzed sample and focused by an infrared lens.

14. Method according to claim 1, wherein the beam is modulated by means of an acousto-optical modulator, or a mechanical chopper, driven by an adjustable generator.

15. Method according to claim 14, wherein the modulated beam signal (MLS) is generated by a light sensor receiving a deviated part of the beam, and wherein the temperature signal (MTS) is generated by an infrared sensor receiving radiation sent out by the heated region or spot of the surface of the analyzed sample and focused by an infrared lens.

16. Method according to claim 15, wherein said light sensor is a photodiode.

17. Method according to claim 15, wherein said deviated part of the beam is light reflected by a lens through which the modulated beam is passing before striking the sample.

18. System for measuring the thermal diffusivity of an object, said system comprising:
   a laser device or a similar heating source whose beam is directed towards a region or spot on a surface of said object,
   means for modulating said laser or heating beam,
   means for generating a signal (MLS) corresponding to said modulated laser or heating beam,
   means for generating a signal (MTS) corresponding to a modulated temperature of the region or spot struck by the modulated beam, and
   amplifying and measuring means able to determine at least one of a phase difference or shift between the modulated beam signal (MLS) and the resulting modulated temperature signal (MTS) and a thermal diffusivity value ($\alpha_m$) of said object based upon said phase shift and associated modulation frequency.

19. System according to claim 18, wherein it is adapted to perform a thermal diffusivity measurement method comprising:
   subjecting a surface region of an object, whose thermal diffusivity ($\alpha_m$) has to be determined, to a modulated laser beam or to a modulated beam of a similar heating source while providing a signal (MLS) thereof, a heated spot or area of the surface of the object having a definitive diameter and a fixed intensity distribution profile;
   providing a signal (MTS) proportional to a temperature on the heated spot or area;
   determining a phase difference or phase shift between the modulated beam signal (MLS) and the resulting modulated temperature signal (MTS);
   using said determined phase difference or shift and an associated modulation frequency to work out the thermal diffusivity value (am) of said object.

* * * * *